US005674858A

United States Patent [19]

McColm

[11] Patent Number: 5,674,858
[45] Date of Patent: Oct. 7, 1997

[54] MEDICAMENTS FOR TREATING GASTROINTESTINAL DISORDERS

[75] Inventor: Andrew Alexander McColm, Greenford, Great Britain

[73] Assignee: Glaxo Group Limited, Great Britain

[21] Appl. No.: 462,586

[22] Filed: Jun. 5, 1995

Related U.S. Application Data

[63] Continuation of Ser. No. 357,223, Dec. 12, 1994, abandoned, which is a continuation of Ser. No. 54,085, Apr. 30, 1993, abandoned, which is a continuation of Ser. No. 946,576, Sep. 18, 1992, abandoned.

[30] Foreign Application Priority Data

Sep. 20, 1992 [GB] United Kingdom .................. 9120131

[51] Int. Cl.$^6$ .......................... A61K 31/65; A61K 31/70; A61K 31/61; A61K 31/555
[52] U.S. Cl. .................. 514/154; 514/29; 514/152; 514/163; 514/184; 514/192; 514/198; 514/199; 514/200; 514/390; 514/398; 514/503; 514/927
[58] Field of Search .................. 514/152, 184, 514/503, 927, 29, 163, 192, 199, 198, 200, 390, 398, 154

[56] References Cited

U.S. PATENT DOCUMENTS

| | | |
|---|---|---|
| 5,008,256 | 4/1991 | Clitherow . |
| 5,128,140 | 7/1992 | Chapura et al. . |
| 5,196,205 | 3/1993 | Borody . |
| 5,256,684 | 10/1993 | Marshall . |

FOREIGN PATENT DOCUMENTS

| | | |
|---|---|---|
| A10302/92 | 3/1992 | Australia . |
| 772567 | 4/1957 | United Kingdom . |

OTHER PUBLICATIONS

Journal of Antimicrobial Chemotherapy (1988) 22, 631–636.

*Primary Examiner*—Raymond Henley, III
*Attorney, Agent, or Firm*—Graham & James LLP

[57] ABSTRACT

The use is described of both (i) ranitidine bismuth citrate and (ii) one or more *Helicobacter pylori*-inhibiting antibiotics in treating or preventing gastrointestinal disorders.

Pharmaceutical compositions containing both (i) and (ii) and methods for the preparation of pharmaceutical compositions containing (i) and (ii) are also described.

22 Claims, No Drawings

MEDICAMENTS FOR TREATING GASTROINTESTINAL DISORDERS

This is a continuation of Ser. No. 357,223 filed Dec. 12, 1994, abandoned, which is a continuation of application Ser. No. 08/054,085, filed Apr. 30, 1993, now abandoned, which is a continuation of application Ser. No. 07/946,576, filed Sep. 18, 1992, now abandoned.

The present invention relates to improvements in the treatment of gastrointestinal disorders. More particularly it relates to the co-administration of a salt formed between ranitidine and a complex of bismuth with a carboxylic acid, with antibiotics.

In our published UK Patent Specification No. 2220937A we describe and claim salts formed between ranitidine and a complex of bismuth with a carboxylic acid, particularly tartaric acid and, more especially, citric acid. One such salt is N-[2-[[[5-[(dimethylamino)methyl]-2-furanyl]methyl]thio]ethyl]-N'-methyl-2-nitro-1,1-ethenediamine 2-hydroxy-1,2,3-propanetricarboxylate bismuth $(3^+)$ complex, also known as ranitidine bismuth citrate.

The salts disclosed in UK Patent Specification No. 2220937A possess the $H_2$-antagonist antisecretory properties associated with ranitidine, together with antibacterial activity against *Helicobacter pylori* (formerly *Campylobacter pylori*). In addition, such salts possess cytoprotective properties, and display activity against the human gastric pepsins, with preferential inhibition of pepsin 1, a pepsin isozyme associated with peptic ulcer. The salts disclosed in UK Patent Specification No. 2220937A thus possess a particularly advantageous combination of properties for the treatment of gastrointestinal disorders, especially peptic ulcer disease and other gastroduodenal conditions, for example gastritis and non-ulcer dyspepsia.

We have now shown that the antibacterial activity of ranitidine bismuth titrate against Helicobacter organisms may be significantly enhanced by co-administering the compound with one or more antibiotics.

The present invention thus provides, in one aspect, the use of (i) ranitidine bismuth citrate and (ii) one or more *Helicobacter pylori*-inhibiting antibiotics in the manufacture of medicaments for simultaneous, separate or sequential use in treating or preventing gastrointestinal disorders.

The term "gastrointestinal disorder" as used herein encompasses a disease or other disorder of the gastrointestinal tract, including for example a disorder not manifested by the presence of ulcerations in the gastric mucosa (eg gastritis, non-ulcer dyspepsia, esophagal reflux disease and gastric motility disorders), and peptic ulcer disease (eg gastric and duodenal ulcer disease).

The ranitidine bismuth citrate is preferably co-administered with one or two antibiotics but, in particularly difficult cases, three antibiotics may be required.

A wide variety of antibiotics may be used according to the invention, including for example nitroimidazole antibiotics (e.g. tinidazole or metronidazole), tetracyclines (e.g. tetracyclin, doxycyclin and minocyclin), pencillins (e.g. amoxycillin, ampicillin and mezlocillin), cephalosporins (e.g. cefachlor, cefadroxil, cephradine, cefuroxime, cefuroxime axetil, cephalexin, cefpodoxime proxetil, ceftazidime and ceftriaxone), carbopenems (e.g. imipenem and meropenem), amino-glycosides (e.g. paromonycin), macrolide antibiotics (e.g. erythromycin, clarithromycin and azithromycin), lincosamide antibiotics (e.g. clindamycin), 4-quinolones (e.g. ofloxacin, ciprofloxacin, pefloxacin and norfloxacin), rifamycins (e.g. rifampicin), nitrofurantoin and derivatives of 10-(1-hydroxyethyl)-11-oxo-1-azatricyclo [7.2.0.0.3.8]undec-2-ene-2-carboxylic acid described in published European Patent Specification No. 0416953 and published International Patent Specification No. WO92/03437.

Antibiotics which may be administered orally are generally preferred. Examples include metronidazole, tetracyclin (especially as tetracyclin hydrochloride), amoxycillin, cefuroxime axetil and clarithromycin.

Preferred combinations include ranitidine bismuth citrate and metronidazole; ranitidine bismuth citrate and tetracyclin; ranitidine bismuth citrate and cefuroxime axetil; ranitidine bismuth citrate and amoxycillin; ranitidine bismuth citrate and clarithromycin; ranitidine bismuth citrate, metronidazole and amoxycillin; ranitidine bismuth citrate, metronidazole and tetracyclin; and ranitidine bismuth citrate, tetracyclin and clarithromycin.

Combinations of ranitidine bismuth citrate and cefuroxime and ranitidine bismuth citrate, cefuroxime and metronidazole may also be preferred.

Particularly preferred combinations comprise ranitidine bismuth citrate co-administered with either metronidazole, tetracyclin, metronidazole and amoxycillin, or metronidazole and tetracyclin. Such combinations have shown a synergistic antibacterial effect against *Helicobacter pylori* in vitro and against *Helicobactor mustelae* in vivo in ferrets. Thus, for example, in combination studies in vivo, co-administration of ranitidine bismuth citrate with one or two antibiotics hereinabove has produced a level of antibacterial activity against Helicobacter mustelae which is better than that shown by the active ingredients individually or, in the case of co-administration with two antibiotics, that shown by the two antibiotics together.

The ranitidine bismuth citrate and the one or more antibiotics are preferably co-administered in the form of separate pharmaceutical compositions for simultaneous and/or, sequential use. Alternatively the ranitidine bismuth citrate and the antibiotic(s) may be administered as a single pharmaceutical composition for oral use comprising effective mounts of the active ingredients.

Thus, according to a further aspect, the invention provides a product containing (i) ranitidine bismuth citrate and (ii) one or more *Helicobacter pylori*-inhibiting antibiotics as a combined preparation for simultaneous, separate or sequential use in treating or preventing gastrointestinal disorders.

When the ranitidine bismuth citrate and the one or more antibiotics are administered as separate preparations, each of the antibiotics may conveniently be provided in the manner known in the an and/or commercially for the compounds concerned. Administration of both the ranitidine bismuth citrate and the antibiotic(s) by the oral route is preferred, although the antibiotic(s), where appropriate, may also be given by another route, for example parenterally (e.g. intravenously, intramuscularly or subcutaneously).

The ranitidine bismuth citrate may conveniently be formulated as tablets (including chewable tablets), capsules (of either the hard or soft type), or as a liquid preparation, as described for example in UK Patent Specification Nos. 2220937A and 2248185A. Tablets are generally preferred.

As stated hereinabove, ranitidine bismuth citrate and the antibiotic(s) may be administered as a single pharmaceutical composition for oral use. Thus according to a further aspect the invention provides a pharmaceutical composition, for oral use in human or veterinary medicine, comprising ranitidine bismuth citrate and one or more *Helicobacter pylori*-inhibiting antibiotics. Such compositions may be formulated in a conventional manner using additional pharmaceutically acceptable carriers or excipients as appropriate. Thus, the composition may be prepared by conventional means with additional careers or excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrates (e.g. starch or sodium starch glycollate); or wetting agents e.g. sodium lauryl sulphate). An alkaline salt of the type described in UK Patent Specification No. 2248185A may be added to improve the rate of disintegration and/or dissolution of the composition. Tablets may be coated by methods well known in the art. The preparations may also contain flavouring, colouring and/or sweetening agents as appropriate.

The compositions may be prepared according to conventional techniques well known in the pharmaceutical industry. Thus, for example, the ranitidine bismuth citrate and the antibiotic(s) may be admixed together, if desired, with suitable excipients. Tablets may be prepared, for example, by direct compression of such a mixture. Capsules may be prepared by filling the blend along with suitable excipients into gelatin capsules, using a suitable filling machine.

When ranitidine bismuth citrate and the antibiotic(s) are administered as a single pharmaceutical composition for oral use the composition is preferably in the form of a capsule or, more particularly, a tablet.

Low packing density oral pharmaceutical compositions comprising a soluble bismuth-containing pharmaceutical agent, including ranitidine bismuth citrate, optionally also comprising a *Helicobacter pylori*-inhibiting antibiotic were recently described in International Patent Specification No. WO92/11849. Thus, according to a further aspect, the present invention provides a pharmaceutical composition for oral use comprising ranitidine bismuth citrate and one or more *Helicobacter pylori*-inhibiting antibiotics wherein the packing density of the composition is not less than 1 g/ml.

The compositions for use according to the invention may, if desire& be presented in a pack or dispenser device which may contain one or more unit dosage forms containing the active ingredients. The pack may for example comprise metal or plastic foil, such as a blister pack. Where the ranitidine bismuth citrate and the one or more antibiotics are intended for administration as separate compositions these may be presented in the form of, for example, a multiple (e.g. twin) pack.

Thus, according to a further aspect the present invention provides a multiple-container pack for use in treating or preventing gastrointestinal disorders, one of the containers containing ranitidine bismuth citrate and the other(s) containing a *Helicobacter pylori*-inhibiting antibiotic.

The doses at which the ranitidine bismuth citrate and the one or more antibiotics may be administered to man (of approximately 70 kg body wight) will depend on the route of administration of the antibiotic and on the nature and severity of the condition being treated. It will also be appreciated that it may be necessary to make routine variations to the dosage depending on the age and weight of the patient.

A proposed dosage of ranitidine bismuth citrate for use according to the invention is 150 mg to 1.5 g, preferably 200–800 mg per unit dose. The unit dose may be administered, for example, 1 to 4 times per day.

The one or more antibiotics may conveniently be administered at doses within the normal dosage range at which the compound(s) are therapeutically effective, or at higher doses if required. The antibiotic(s) may be taken one or more times daily as appropriate.

In a further aspect, the present invention provides a method for treating or preventing gastrointestinal disorders in a human or animal subject, which comprises administering to said subject effective amounts of ranitidine bismuth citrate and one or more *Helicobacter pylori*-inhibiting antibiotics.

The methods of the present invention comprise administering the *Helicobacter pylori*-inhibiting antibiotic(s) and ranitidine bismuth citrate either concurrently or non-concurrently. As used herein, concurrent administration means that the agents are given within 24 hours of each other, whereas non-concurrent administration means that the agents are given more than 24 hours apart. When the agents are administered concurrently, it may be preferable to administer the agents within about 1 hour of each other or, more preferably, within about 5 minutes of each other.

For the methods of the present invention, the duration of administration of the agents during either concurrent or non-concurrent dosing will vary according to the specific gastrointestinal disorder being treated. However, a typical regime would be to administer ranitidine bismuth citrate for 4 to 8 weeks and during this period to administer one or more antibiotics for 1 to 2 weeks.

As stated hereinabove, certain combinations of ranitidine bismuth citrate with antibiotics have shown a synergistic effect in vitro against Helicobacter pyloriand in vivo against *Helicobacter mustelae*.

In Vitro Synergy Methodology

Synergy was measured dependent on the rate of kill observed in minimal bactericidal concentrations (MBCs) using a 2-dimensional microtitre checkerboard method[1]. The checkerboard is produced by serially diluting agent A prior to addition to the plates. Agent B was then diluted in the wells containing A to a final volume of 50 µl. Each well is then inoculated with 50 µl of *H. pylori* cultured in broth and the plates incubated at 37° C. Plates are then sampled at 24, 48 and 72 hours for *H. pylori* growth using a 0–6 quantitative scale. Mean fractional inhibitory concentrations (FICs) were then determined from 2-dimensional isobolograms. A mean FIC index of less than 1=synergy[2].

To confirm synergy, time kill studies using the apparently effective combinations were subsequently performed in 3 ml broth cultures.

$$\text{where } FIC_A = \frac{MBC_A \text{ in presence of } B}{MBC_A}$$

$$\text{and } FIC_B = \frac{MBC_B \text{ in presence of } A}{MBC_B}$$

In Vivo Synergy Methodology

Ferrets naturally colonised with *H. mustelae* were treated with either ranitidine bismuth citrate (24 mg/kg), amoxycillin and metronidazole (10 mg/kg and 20 mg/kg respectively) or the combination of all three agents. Compounds were given orally three times daily for 28 days with the exception of metronidazole (day 0–9 only). The apparent colonisation frequency was assessed from gastric antral biopsies obtained by endoscopy before, during and after the therapy phase. A culture—positive biopsy means that the compound is still colonised.

Results

In vitro the combination of ranitidine bismuth citrate with tetracyclin, metronidazole, amoxycillin or cefuroxime demonstrated a synergistic effect. Indeed, the combination of ranitidine bismuth citrate with tetracyclin or metronidazole gave a mean HC index<0.5.

In vivo, the combination of ranitidine bismuth citrate with metronidazole and amoxycillin proved superior to either ranitidine bismuth citrate alone or the antibiotics alone and lead to ⅚ infections being eradicated. The ranitidine bismuth citrate or antibiotic alone groups failed to eradicate but showed good suppression. The removal of metronidazole from the regime after ten days dosing resulted in a subsequent relapse of infections by day 28, particularly in the metronidazole/amoxycillin group.

References

1. Berenbaum, M. C. The Journal of Infectious Diseases, 137(2) (1978), 122–130.
2. McLaren, A and McDowell, S. R., Irish Journal of Medical Science, 5th Workshop on Gastroduodenal Pathology and *Helicobacter pylori*, p98 (1992).

I claim:

1. A method for treating gastrointestinal disorders caused or mediated by *H. pylori* infections in humans or animals which comprises administering to a human or animal in need thereof an amount of ranitidine bismuth citrate effective against *H. pylori* in combination with a pharmaceutically acceptable carrier, one antibacterial agent selected from the group consisting of metronidazole, amoxycillin and clarithromycin in an amount effective against *H. pylori* in combination with a pharmaceutically acceptable carrier, and one antibiotic selected from the group consisting of tinidazole, tetracyclin, doxycyclin, minocyclin, ampicillin, mezlocillin, cefachlor, cefadroxil, cephradine, cefuroxime, cefuroxime axetil, cephalexin, cefpodoxime proxetil, ceftazidime, ceftriaxone, imipenem, meropenem, paromonycin, erythromycin, azithromycin, clidamycin, ofloxacin, ciprofloxacin, pefloxacin, norfloxacin, rifampicin and nitrofurantoin, in combination with a pharmaceutically acceptable carrier, said ranitidine bismuth citrate and said antibacterial agent being administered in relative amounts such that it provides a greater than additive effect, said administration being concurrent or nonconcurrent.

2. A method according to claim 1 wherein the gastrointestinal disorder treated is a non-ulcerative one.

3. A method according to claim 1 wherein the gastrointestinal disorder treated is gastritis, non-ulcer dyspepsia, esophagal reflux disease or gastric motility disorder.

4. A method according to claim 1 wherein the gastrointestinal disorder treated is peptic ulcer disease.

5. A method according to claim 1 wherein from 150 mg to 1.5 g of ranitidine bismuth citrate is administered one to four times per day.

6. A method according to claim 5 wherein from 200 to 800 mg of ranitidine bismuth citrate is administered one to four times per day.

7. A method according to claim 1 wherein the administration is concurrent.

8. A method according to claim 1 wherein the administration is nonconcurrent.

9. A method according to claim 1 wherein the antibacterial agent is metronidazole and the antibiotic is tetracyclin.

10. A method according to claim 1 wherein the antibacterial agent is clarithromycin and the antibiotic is tetracyclin.

11. A method according to claim 1 wherein the antibacterial agent is metronidazole and the antibiotic is cefuroxime.

12. A method according to claim 1 wherein the administration is oral.

13. A pharmaceutical composition useful for treating gastrointestinal disorders caused or mediated by *H. pylori* infections in humans and animals which comprises an amount of ranitidine bismuth citrate effective against *H. pylori*, one antibacterial agent selected from the group consisting of metronidazole, amoxycillin and clarithromycin in an amount effective against *H. pylori*, one antibacterial agent selected from the group consisting of metronidazole, amoxycillin and clarithromycin in an amount effective against *H. pylori* in combination with a pharmaceutically acceptable carrier, and one antibiotic selected from the group consisting of tinidazole, tetracyclin, doxycyclin, minocyclin, ampicillin, mezlocillin, cefachlor, cefadroxil, cephradine, cefuroxime, cefuroxime axetil, cephalexin, cefpodoxime proxetil, ceftazidime, ceftriaxone, imipenem, meropenem, paromonycin, erythromycin, azithromycin, clidamycin, ofloxacin, ciprofloxacin, pefloxacin, norfloxacin, rifampicin and nitrofurantoin, in combination with a pharmaceutically acceptable carrier, said ranitidine bismuth citrate and said antibacterial agent being present in relative amounts such that the combination provides a greater than additive effect.

14. A pharmaceutical composition according to claim 13 wherein said gastrointestinal disorder is a nonulcerative disorder.

15. A pharmaceutical composition according to claim 13 wherein said gastrointestinal disorder is gastritis, nonulcer dyspepsia, esophageal reflux disease or gastric motility disorder.

16. A pharmaceutical composition according to claim 13 wherein said gastrointestinal disorder is peptic ulcer disease.

17. A pharmaceutical composition according to claim 13 in unit dosage form comprising about 15 mg to 1.5 g of ranitidine bismuth citrate.

18. A pharmaceutical composition according to claim 13 in unit dosage form comprising from about 200 to 800 mg of ranitidine bismuth citrate.

19. A pharmaceutical composition according to claim 13 which is formulated for oral administration.

20. A pharmaceutical composition according to claim 13 wherein the antibacterial agent is metronidazole and the antibiotic is tetracyclin.

21. A pharmaceutical composition according to claim 13 wherein the antibacterial agent is clarithromycin and the antibiotic is tetracyclin.

22. A pharmaceutical composition according to claim 13 wherein the antibacterial agent is metronidazole and the antibiotic is cefuroxime.

* * * * *